(12) United States Patent
Tomlin

(10) Patent No.: US 6,399,391 B1
(45) Date of Patent: Jun. 4, 2002

(54) LOW COST TOTAL REDUCED SULFUR ANALYSIS SYSTEM

(76) Inventor: Robert L. Tomlin, Rte. 3, Box 127, Waldron, AR (US) 72958

( * ) Notice: Subject to any disclaimer, the term of this patent is extended or adjusted under 35 U.S.C. 154(b) by 0 days.

(21) Appl. No.: 08/328,521

(22) Filed: Oct. 25, 1994

(51) Int. Cl.[7] .............................................. G01N 27/00
(52) U.S. Cl. ...................... 436/123; 422/82.01; 422/83; 422/93; 436/102; 436/119; 436/120; 436/122
(58) Field of Search ................................ 436/102, 119, 436/120, 122, 123; 422/82.01, 93, 83

(56) References Cited

U.S. PATENT DOCUMENTS

| | | | |
|---|---|---|---|
| 3,969,626 A | | 7/1976 | Saltzman |
| 4,161,883 A | * | 7/1979 | Laird ......................... 73/421.5 |
| 4,191,541 A | | 3/1980 | Jenkins |
| 4,231,256 A | | 11/1980 | Chapman et al. |
| 4,325,911 A | | 4/1982 | Vincent |
| 4,440,726 A | * | 4/1984 | Coulson |
| 4,484,481 A | * | 11/1984 | Laird ....................... 73/863.12 |
| 4,608,065 A | | 8/1986 | Lai |
| 4,705,669 A | | 11/1987 | Tsuji et al. |
| 4,738,147 A | * | 4/1988 | Tomlin ...................... 73/864.81 |
| 4,740,473 A | * | 4/1988 | Tomlin ......................... 436/79 |
| 5,053,623 A | | 10/1991 | McGowan et al. |
| 5,178,022 A | * | 1/1993 | Tomlin ...................... 73/864.81 |

FOREIGN PATENT DOCUMENTS

DE        3321165        *  8/1984

OTHER PUBLICATIONS

Chemical Abstract 115:222306 "Electochemical gas sensor arrangement with increased sensitivity, stability" Gyulai, DE 3910038 (1995).*
Chemical Abstract 103: 188775 "Sensors for use in gases or gas mixtures" Williams, GB 2149121 (1995).*

* cited by examiner

Primary Examiner—Jan Ludlow
(74) Attorney, Agent, or Firm—Dennison, Sheiner & Schultz

(57) ABSTRACT

A system and apparatus for analyzing stack gas for total reduced sulfur. The gas is withdrawn from a stack through a probe, filtered and regulated to a known temperature. The gas is then passed through a scrubbing column to remove sulfur dioxide and split into first and second portions. The first portion is oxidized to covert total reduced sulfur compounds to $SO_2$, and the gas is then passed to an electrochemical sensor for $SO_2$ which is maintained at a temperature at least equal to the temperature of the regulated gas. The second portion of the scrubbed gas is passed through an electrochemical sensor for oxygen which is maintained at substantially the same temperature as the sensor for $SO_2$.

20 Claims, 5 Drawing Sheets

LOW COST TOTAL REDUCED SULFUR ANALYSIS SYSTEM

BACKGROUND OF THE INVENTION

1. Field of the Invention

This invention relates to a process and apparatus for measuring the gaseous content of industrial process gas streams, in which a portion of the process gas stream is extracted, conditioned for analysis, and analyzed on a gas analysis system using electrochemical gas sensors.

The invention relates more specifically to a gas analysis system for measuring total reduced sulfur (TRS) and other gases, which would meet or exceed the requirements of the U.S. Environmental Protection Agency (EPA), while greatly reducing cost and maintenance requirements of existing systems.

2. Description of Related Art

Total reduced sulfur, is defined by the EPA, to be the sum of hydrogen sulfide methyl mercaptan, dimethyl sulfide and dimethyl disulfide. $SO_2$ is not included. Total reduced sulfur compounds are measured by removing any $SO_2$ that coexists with the TRS gases using an $SO_2$ scrubber, passing the remaining gases through a thermal oxidizer to convert the remaining TRS compounds to $SO_2$, and then analyzing the $SO_2$ using a fluorescence type analyzer.

Existing TRS analyzer systems are very expensive to manufacture, install and maintain. A typical TRS analyzer system contains the following components:

1. A sampling probe/conditioning system that is installed on the boiler or kiln stack;
2. A tubing umbilical to transport the gases to the analyzer location;
3. An air-conditioned shelter for the TRS analysis system;
4. A fluorescence type $SO_2$ analyzer;
5. An $SO_2$ scrubber;
6. A thermal oxidizer;
7. Stainless steel sample pump; and
8. A regenerative air cleanup system.

Existing TRS analyzer systems may cost as much as $50,000.00 and the installation cost can easily double or triple that amount for analyzer shelters and umbilical tubing installation. Maintenance on these systems is complicated because the system may be spread out over 500 feet or more between the sample probe location and the analyzer location. These systems are permanently installed and must be serviced by field technicians. Due to analyzer response time requirements of the EPA and the flow required by the fluorescence type $SO_2$ analyzer, relatively large flows (3000 cc/min) must be pulled from the stack and 400 to 600 cc/min must be supplied to the analyzer. These gas flow rates set the size of the $SO_2$ scrubber, the thermal oxidizer and other system components. These systems have been highly developed over the years and little more can be done to reduce the cost of this type of system.

Attempts to lower the cost of the system by replacing the fluorescence type $SO_2$ analyzer with electrochemical sensors have had limited success. To transport the TRS gases over long distances without sample loss requires the use of a dilution type probe that provides a very dilute (50:1 dilution) gas to the analyzer. Electrochemical $SO_2$ sensors generally have trouble measuring these low concentrations. Another problem is that the electrochemical sensors are damaged by the extremely dry gas supplied by the dilution sampling system. Electrochemical sensors may also be damaged by too much moisture; too little and the sensor dries out, too much and condensation may form inside the sensor causing the sensor to fail. The extremely dry gas also dries out the $SO_2$ scrubber media, which must be back flushed with humidified air every fifteen minutes. The $SO_2$ scrubber distilled water reservoir must be filled at least once each week.

SUMMARY OF THE INVENTION

It is therefore an object of the invention to provide a system for monitoring TRS of relatively lesser size and cost than prior art system.

It is a further object of the invention to provide a system for monitoring TRS utilizing a low-cost electrochemical sensor for $SO_2$.

To achieve these and other objects the invention provides a TRS analyzer and gas conditioning system that is advantageously contained in one enclosure at the stack location. The system includes a sampling probe for withdrawing stack gas, a filter for removing particulate matter from withdrawn stack gas, a heat exchanger for precisely regulating the temperature of the filtered gas, a scrubbing column for removing $SO_2$ from the temperature regulated gas, splitting means for splitting the scrubbed gas into two portions, an oxidizer for oxidizing a first portion of the scrubbed gas to covert total reduced sulfur compounds to $SO_2$, a first electrochemical sensor for determining $SO_2$ in the converted gas, a second electrochemical sensor for determining oxygen in a second gas portion, and means for regulating the temperature of the first and second sensors to a value substantially the same and which is at least equal to the temperature of the heat exchanger. This system does not require a tubing umbilical, air-conditioned shelters, sample pumps or regenerative air dryers. The entire system can be contained in a 24"W×30"W×8"D enclosure and weigh 65 pounds. This TRS analyzer can be manufactured at a much lower cost and requires less maintenance.

The TRS system of the invention was designed to solve the problems associated with using electrochemical sensors to measure TRS and $O_2$. This system uses low flow rates to allow for long sample filter life and to allow all gas conditioning components to be miniaturized to reduce cost. Installing the analyzers at the stack location eliminates the need for a tubing umbilical. Locating the analyzers close to the source also allows the analyzers to respond quickly even with low sample flow rates.

The invention also provides a method for analyzing gas flowing through a stack for total reduced sulfur comprising the steps of withdrawing a portion of the gas flowing through the stack, filtering the withdrawn gas, regulating the temperature of the filtered gas to a predetermined value, scrubbing $SO_2$ from the temperature regulated gas in a column at substantially the same temperature as the regulated gas, splitting the scrubbed gas into first and second portions, oxidizing a first a first portion of the scrubbed gas to convert total reduced sulfur compounds to $SO_2$, analyzing the converted gas for $SO_2$ with an electrochemical sensor maintained at a temperature at least equal to the regulated gas, and analyzing the second portion of the scrubbed gas for oxygen utilizing a second electrochemical sensor maintained at a temperature at least equal to the regulated gas and which is substantially the same as the first sensor.

By measuring the stack gas directly, without dilution, and installing the $SO_2$ scrubber into the same temperature controlled zone as the heat exchanger, the need for water addition to the scrubber has also been eliminated. By placing the electrochemical sensors into a separate temperature controlled zone and controlling the temperature difference between the gas heat exchanger and electrochemical sensors, precise control over the humidity level of the gas can be maintained. This allows the electrochemical sensors to operate long term with minimum drift.

BRIEF DESCRIPTION OF THE DRAWINGS

FIG. 3A is a top view of the heat exchanger—$SO_2$ scrubber shown in FIG. 3;

DESCRIPTION OF THE PREFERRED EMBODIMENTS

Figure 1:
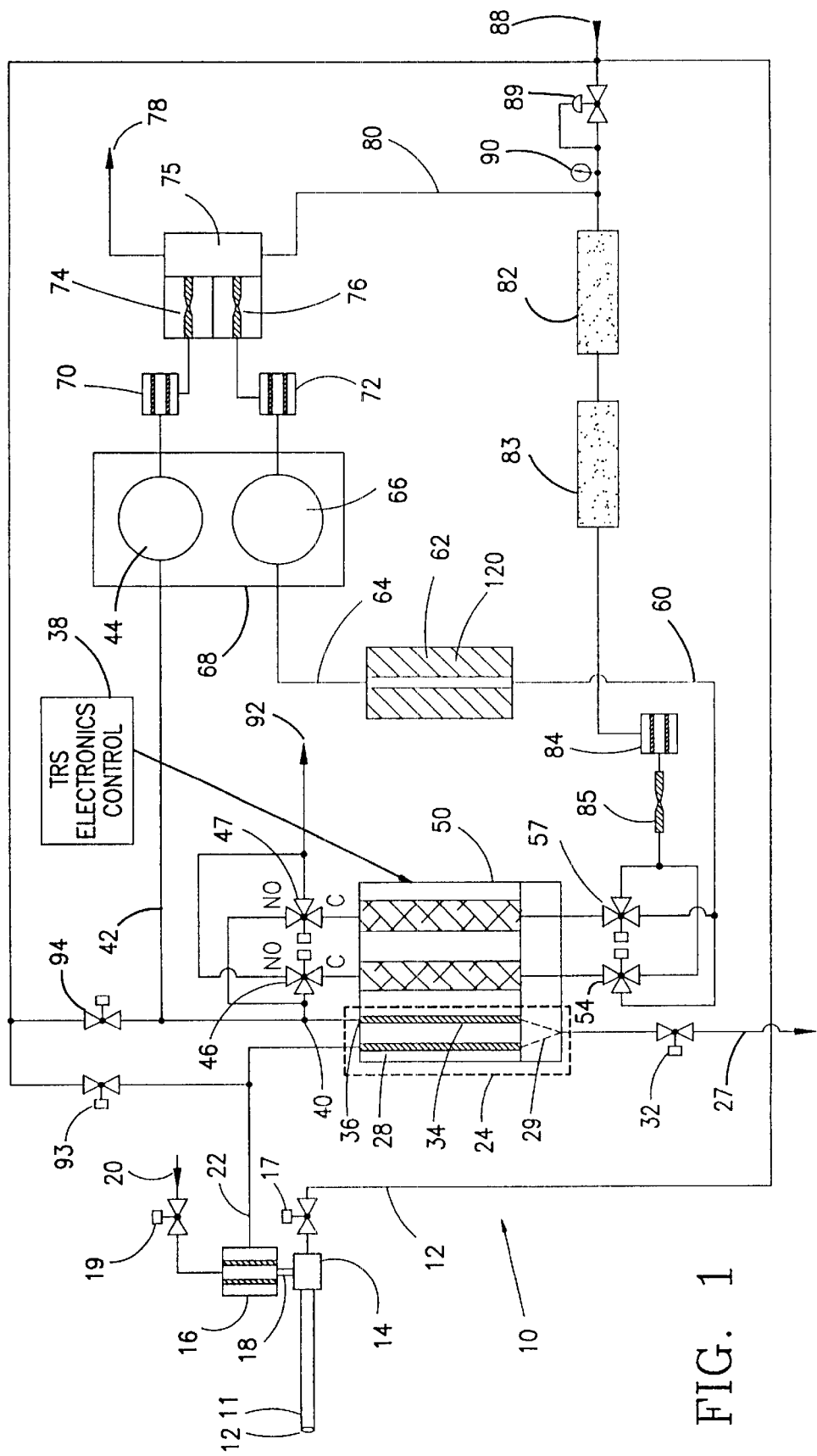
FIG. 1 is a schematic diagram of the TRS monitoring system of the invention.
Figures 2, 2A:
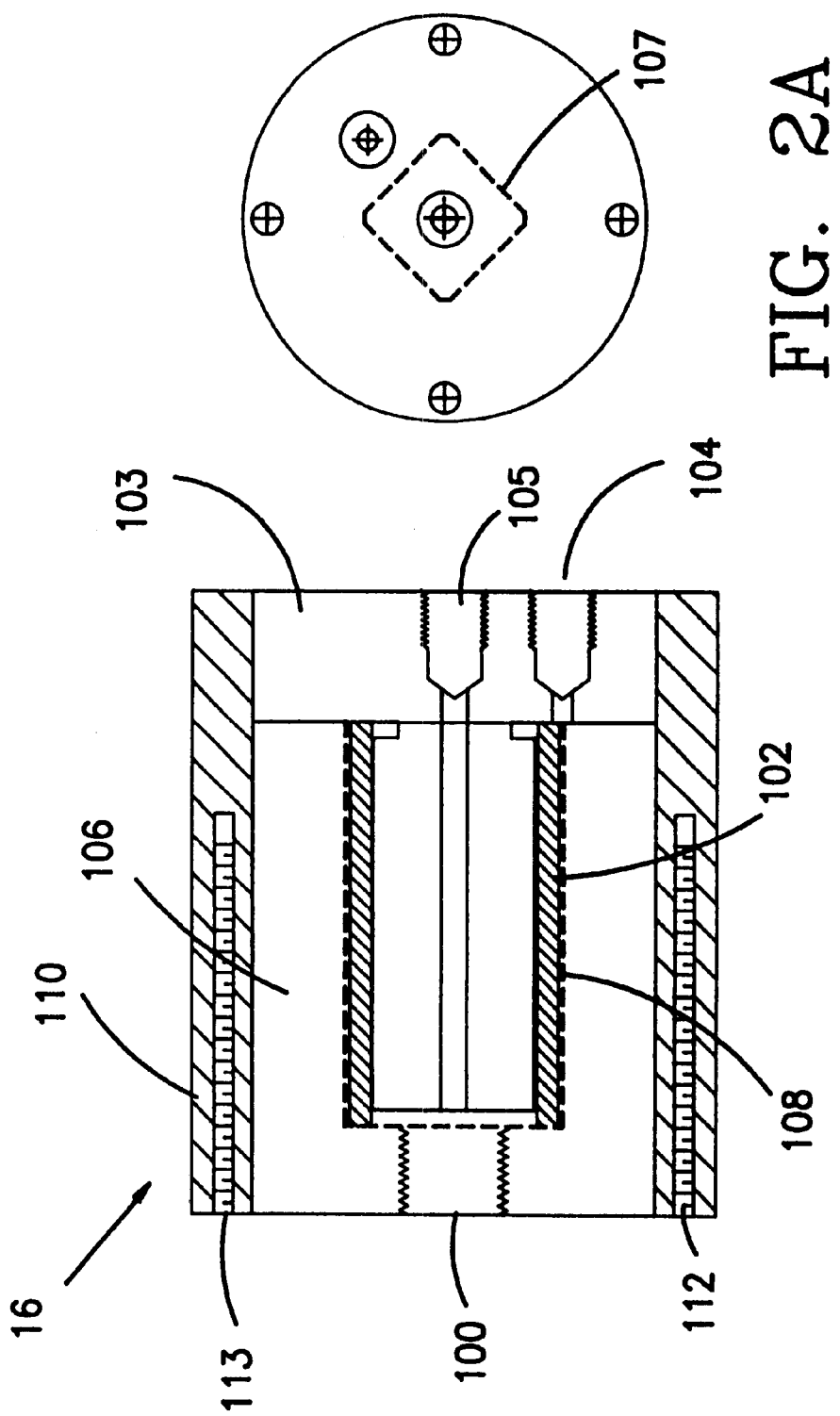
FIG. 2 is a cross-sectional view of the heated sample filter shown in FIG. 1.
FIG. 2A is an end view of the sample filter of FIG. 2.

As shown in FIG. 1, the system 10 of the invention includes a probe 11 having a probe tip 12 for insertion in the stack containing the gas to be monitored. The probe 11 may be fabricated from any material compatible with the stack gases, but is usually Hastelloy C-276 for recovery boilers and Hastelloy C-276 with a teflon liner for lime kilns. At the rear end of the probe is a transition block 14 constructed of Torlon which functions to connect the sample probe with heated filter 16 or with blowback valve 17. A Torlon nipple 18 connects the transition block to the heated filter 16, which is shown in greater detail in FIGS. 2 and 2A. Heated filter 16 includes a sample entrance 100 directing gas to a glass fiber filter element 102 and through sample exit port 104 in end cap 103, also containing port 105. The filter body 106 is manufactured from TFE teflon, and end cap 103 has a square mandrel 107 that reduces the internal volume of the filter. Square mandrel 107 only touches the filter element 102 at the corners and does not appreciably reduce the available filter surface area. Filter dead volume is further reduced by making the gap 108 between the filter element and the filter body as small as possible, gap 108 being approximately 0.050 inches. Reducing the volume of the filter in this manner improves the response time of the sampling system by reducing dead volume. The filter body 106 and end cap 103 are enclosed in a heated filter housing 110 manufactured from aluminum and heated by a cartridge heater 112 with a temperature sensed by a temperature sensor 113, both located in the heated filter housing 110.

Figure 3:
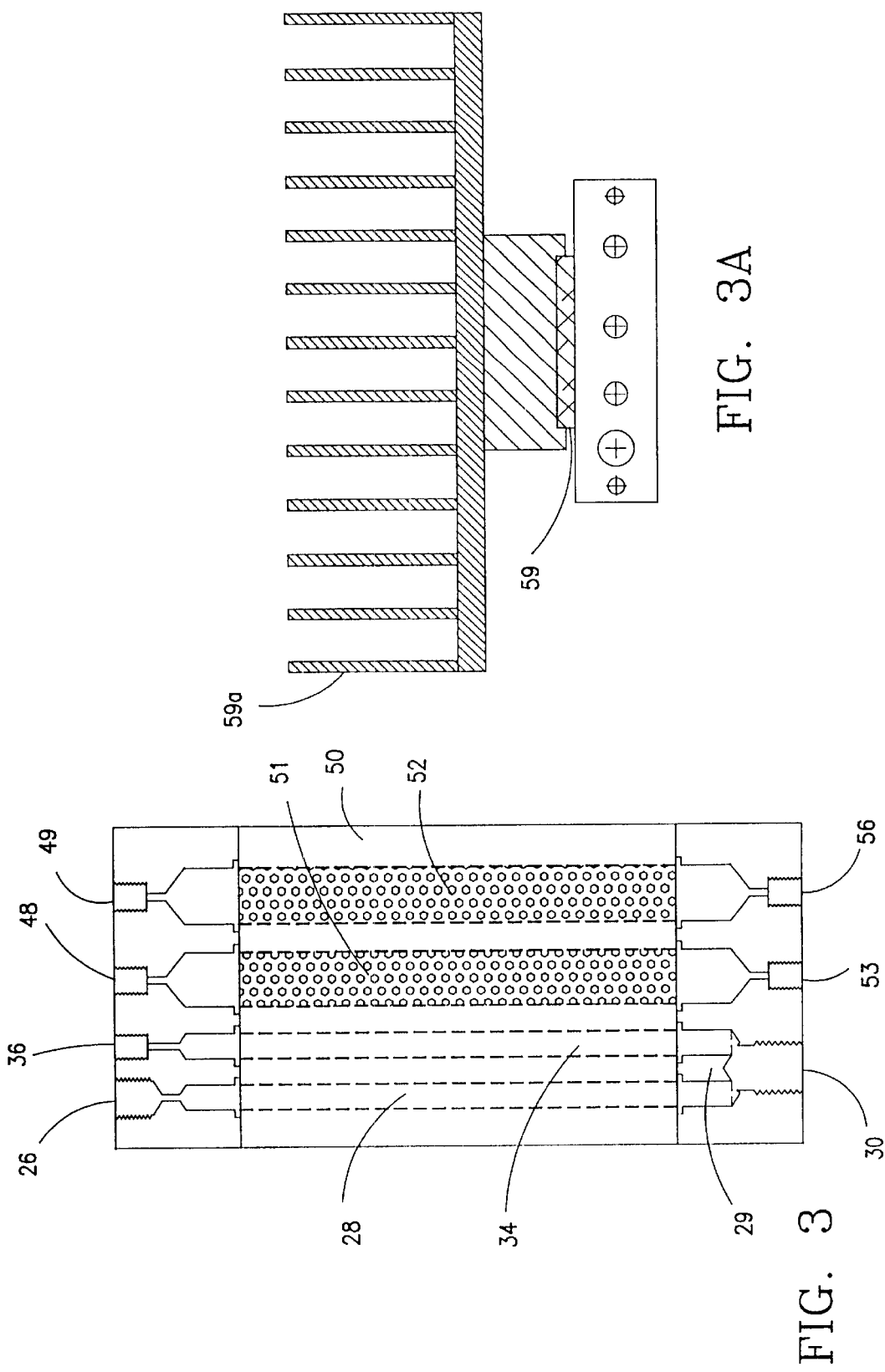
FIG. 3 is a cross-sectional view of a combination heat exchanger $SO_2$ scrubber shown in FIG. 1.

Port 105 is connected to a valve 19, and then to a source of calibration gas 20. Exit port 104 in the heated filter is connected by way of line 22 to a heat exchanger 24 formed as an assembly with an $SO_2$ scrubber 50, both shown in greater detail in FIGS. 3 and 3A. The heat exchanger includes a sample entrance port 26 and a teflon exchanger tube 28 with a reservoir section 29 at the bottom thereof. The reservoir section 29 collects water condensed from the sample gas. Any water collected flows out through port 30 and through a drain valve 32. The sample flows upwardly through teflon tube 34 and out of the heat exchanger through port 36. The temperature of the heat exchanger is controlled by the TRS electronics control 38, and may be set between 35 and 90° F., preferably at 50° F.

The filtered and dried stack gas exiting through port 36 is then split into two portions at splitter 40. A first flow proceeds through line 42 to oxygen analyzer 44. The remainder of the flow is directed to parallel scrubber valves 46 and 47. The output of valve 46 is connected to input 48 of $SO_2$ scrubber 50 while the output of valve 47 is connected to input 49 of the $SO_2$ scrubber. $SO_2$ scrubber 50 is formed as a unit with the heat exchanger and includes parallel scrubber columns 51 and 52. Columns 51 and 52 are teflon tubes containing the $SO_2$ scrubber media; forming the scrubber units in the same housing as the heat exchanger causing the sample gas flowing through the $SO_2$ scrubber media to be at the same relative humidity and temperature as the gas leaving the heat exchanger. The high relative humidity in the $SO_2$ scrubber columns prevents the scrubber material from drying out and thereby affecting the response time of the TRS gases flowing through the scrubber.

The unit is cooled by thermoelectric cooler 59 and heat is dissipated from the heat exchanger by heat sink 59a.

Scrubbed sample gas flowing outwardly through column 51 exits at port 53 and is directed to a valve 54; scrubbed sample gas exits column 52 at port 56 and flows to a valve 57. By appropriately energizing the valves 46, 47, 54 and 57, it is possible to utilize one column for scrubbing $SO_2$ while the other column is scrubbed of absorbed sulfur containing compounds.

Figure 4:
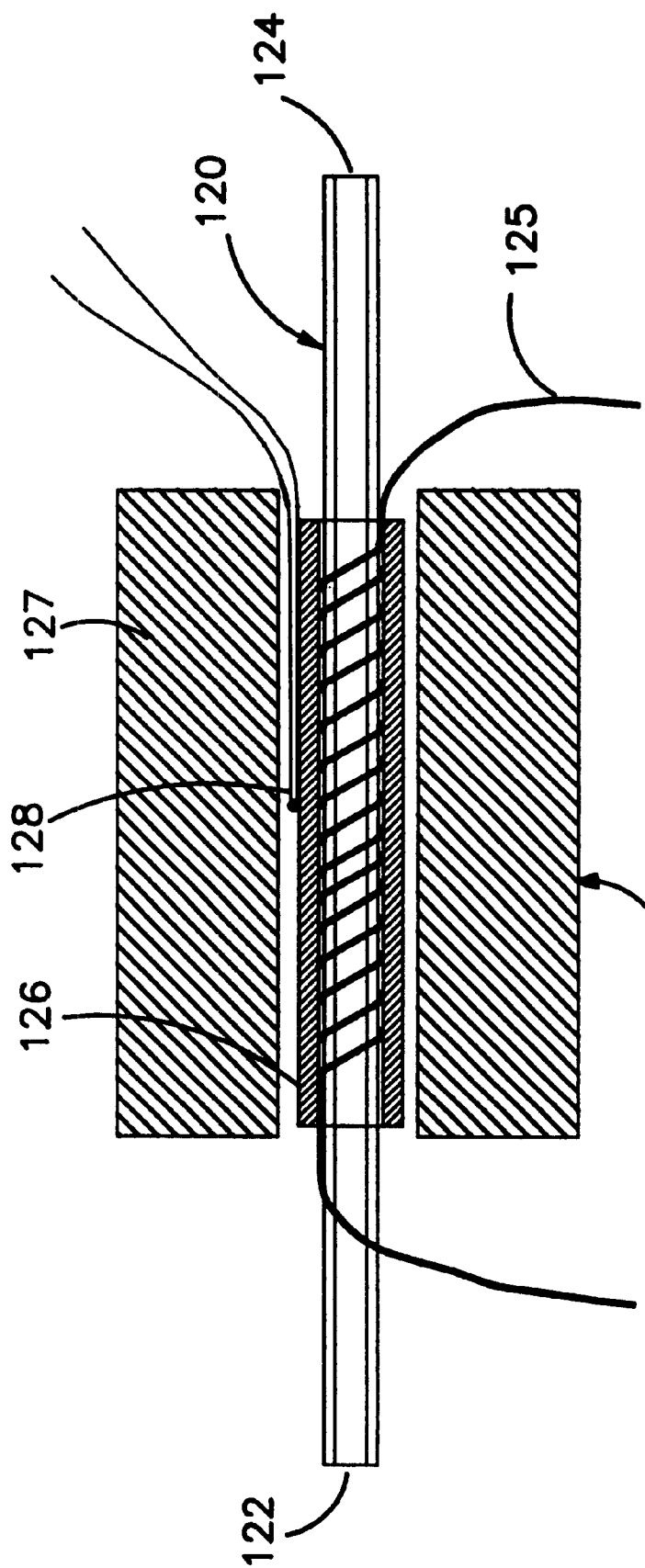
FIG. 4 is a cross-sectional view of a thermal oxidizer shown in FIG. 1.

Scrubbed sample gas is directed through line 60 to thermal oxidizer 62, shown in greater detail in FIG. 4. The thermal oxidizer includes a quartz tube 120 through which the sample flows from an inlet port 122 to an outlet port 124. The quartz tube is heated to 1200° F. by a low voltage Tophet heater 125. Heater 125 is protected by quartz protection sleeve 126 and insulated with a ceramic fiber blanket 127. The internal heated volume of the oxidizer is 0.7 cc. Oxidizer temperature is sensed by thermocouple 128 which is connected to TRS electronics control 38.

Figures 5, 5A:
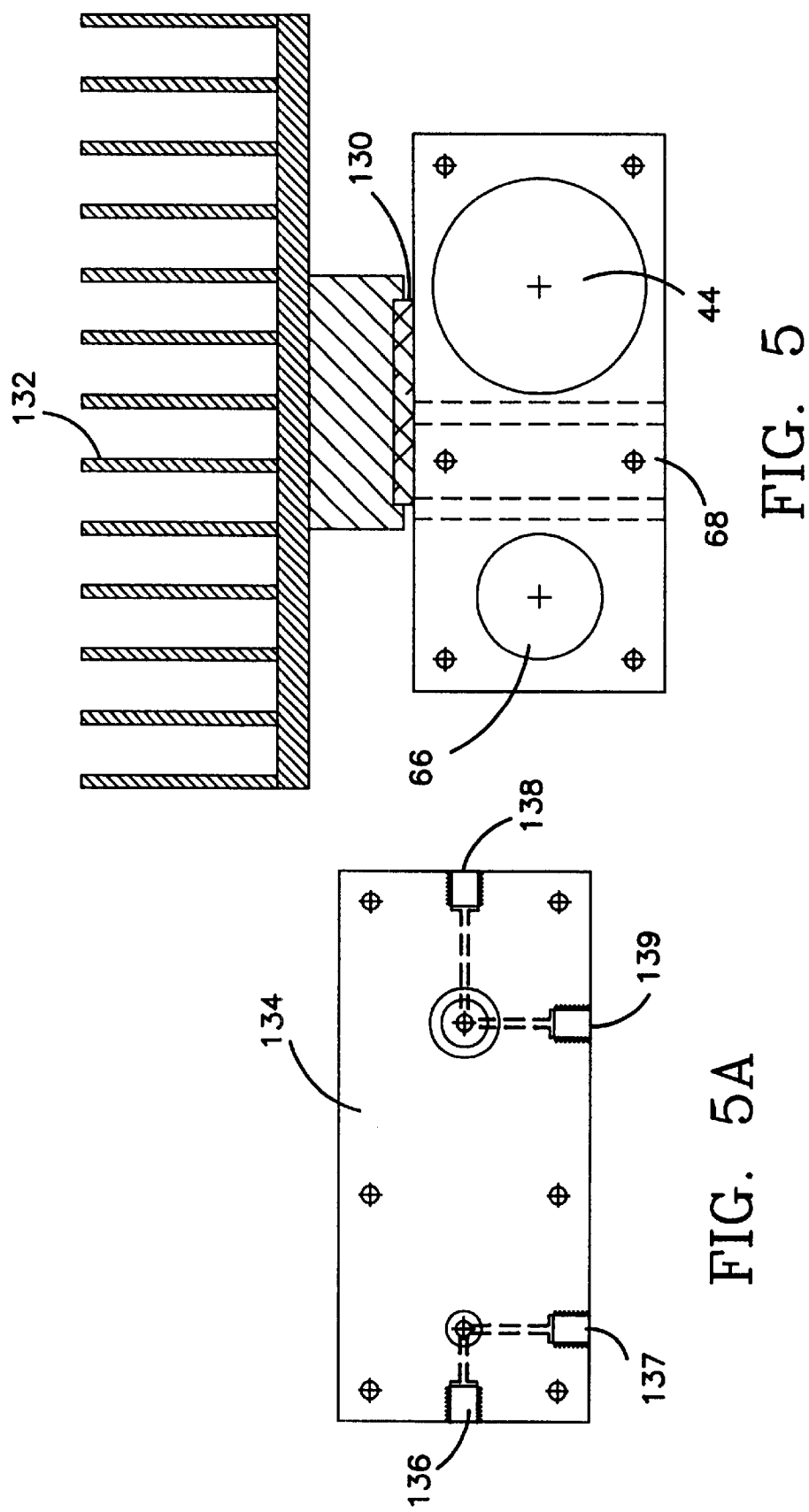
FIG. 5 is a top view of a thermoelectric sensor heating block shown in FIG. 1.
FIG. 5A is a top view of a housing manifold for the sensor block of FIG. 5.

Oxidized sample gas passes through line 64 to the $SO_2$ electrochemical sensor 44 installed into a teflon manifold embedded into aluminum housing 68, which also contains oxygen sensor 66. The housing is shown in detail in FIGS. 5 and 5A, and includes a thermoelectric cooler 130 and heat sink 132 to provide a thermal path from the cooler to the outside ambient air.

Sensor housing 68 sits on top of a manifold 134 formed from TFE teflon and designed to reduce dead volume to a minimum. Sample gas enters the $O_2$ cell through a port 136 and exits through a port 137, while sample gas enters the $SO_2$ cell at port 138 and exits through port 139.

The sensor housing includes a temperature sensor which is connected to TRS electronics control 38.

The gas exiting the sensors flow through orifice protection filters 70 or 72, and then to eductor 75, through tubes 74 or 76. The gas flowing through the sensors is vented at 78. The eductor utilizes instrument gas provided for the blowback circuit through source 88, pressure regulated by regulator 89 and gauge 90. For scrubber back flush purposes, the circuit includes a charcoal filter 82, potassium permanganate filter 83, particulate filter 84 and back flush orifice 85, which is connected to the outlet valves from the scrubber columns. After cleaning the columns, the gas is vented at port 92, which is connected to the inlet valves for the scrubber columns.

Other elements of the system can also be cleaned by the instrument gas in blowback mode. In particular, the instrument gas is connected to the transition block 14 through valve 17, and the heat exchanger through valves 93 and 94.

Operation of the System

Stack gas containing TRS compounds enters the analysis system at tip 12 of probe 11. Stack gas is drawn through the probe at a flow rate of 50 cc/min, and from the probe the stack gas flows into the transition block 14. From the transition block 14, the gas flows through the Torlon nipple 18 into filter 16, which is heated to 300° F. to prevent sample loss on the glass fiber filter element. Alternatively, calibration gas can enter the heated filter through valve 19, permitting the gas to flow through the same path as the stack gas and detect any losses in the sampling system. Blowback valve 17 is provided periodically to clean the probe by allowing high pressure air from inlet 88 to blow accumulated particulate matter back into the stack. This air usually has a pressure of 60 to 90 psig.

From the heated filter, the filtered stack gas flows through line 22 into heat exchanger 24, which removes the water from the stack gas to provide a dry basis measurement, as required by the EPA. Gas flows through the heat exchanger tubes 28 and 34 in series, connected at the bottom by a teflon liquid reservoir 29. The heat exchanger is thermoelectrically cooled to a temperature between 35 and 90° F., and preferably 50° F., with control by the TRS electronics control 38. Condensate collected in the heat exchanger drains into the reservoir 29 and is drained periodically through drain valve 32. Drain valve 32 can be energized automatically every 15 minutes by the TRS electronics control.

Exchanger purge valves 93 and 94 are provided to force condensate out the drain valve during the probe blowback. Blowback valve 17, exchanger purge valve 93 and exchanger purge valve 94 and drain valve 32 are all energized simultaneously for the blowback cycle, which can last approximately 5 seconds.

From the heat exchanger, the filtered and dried stack gas flows to point 40, where the gas stream splits into two equal flows, typically 25 cc/min. Because the electrochemical sensors are not flow sensitive, exact flow rates are not important and the flow rate of 25 cc/min was chosen as a good compromise between filter life, $SO_2$ scrubber life, response time and cost to manufacture. Flows between 5 and 100 cc/min can also be used depending on the application.

From point 40, a stack gas flow of 25 cc/min flows into scrubber valves 46 and 47. With the $SO_2$ scrubber valves de-energized, the stack gas flows through valve 47 through scrubber column 52 and through exit valve 57 into the thermal oxidizer unit. While $SO_2$ scrubber column 52 is being used, scrubber column 51 is being back flushed to vent with filtered instrument air which enters the system at point 88, and flows through pressure regulator 89 and gauge 90. Pressure regulator 89 is used to set the correct operating pressure of 30 psig for the sample eductor 75 used to vent the gases after analysis and the $SO_2$ scrubber back purge orifice 85. From the pressure regulator, the instrument air flows through the charcoal filter 82 and potassium permanganate filter 83, provided to insure that the instrument air is scrubbed of any sulfur compounds that could conceivably contaminate the $SO_2$ scrubber columns. The air then flows through particulate filter 84 and scrubber back flush orifice 85, which sets the back flush flow at 250 cc/min, or ten times the normal forward flow of 25 cc/min. Setting the flows in this manner insures that the $SO_2$ scrubber column will be completely regenerated before the start of each measurement cycle. After 15 minutes, the TRS electronics control 38 automatically energizes all four scrubber valves 46, 47, 54 and 57 simultaneously, causing column 51 to become the active column and column 52 to go into the back flush mode. The TRS electronics control 38 also causes a 5 second blowback/heat exchange purge cycle at the time of scrubber switching. The control holds both analyzer outputs constant for three minutes after a blowback/purge cycle.

The $SO_2$ scrubber is located in the same aluminum housing as the heat exchanger such that the stack gas leaving the heat exchanger has a dew point of 50° F. or a relative humidity of 100% at 50° F. If the $SO_2$ scrubber were allowed to operate at prevailing ambient temperatures between −20° F. and 122° F., the scrubber columns would be getting wetter at temperatures below 50° F. and drier at temperatures above 50° F. Precise control of the $SO_2$ temperature and humidity is a key factor to obtaining a reliable and accurate output from the TRS analyzer. By installing the $SO_2$ scrubber in the same block as the heat exchanger, the $SO_2$ scrubber is kept under the correct moisture conditions that allow efficient scrubbing of $SO_2$ without losing the TRS compounds.

The scrubber material must be acidic to allow the passage of the TRS gases. It is desirable to operate the scrubber in the range of 50 to 100% relative humidity to maintain the correct scrubber pH and prevent the loss of TRS gases on the scrubber material. Operating the $SO_2$ scrubber in this manner eliminates the need to add distilled water to the analyzer on a weekly basis, and eliminating the distilled water reservoir also eliminates the need for heating the enclosure to prevent the water from freezing. Controlling the $SO_2$ scrubber temperature will also give much more consistent output than existing systems that allow the scrubber temperature to vary with the enclosure temperature.

From the $SO_2$ scrubber, the filtered, dried and scrubbed stack gas flows to thermal oxidizer 62, which operates at a temperature of 1200° F. The thermal oxidizer tube 120 is made of quartz glass and is generally of dimensions 0.250 inches OD×0.150 inches ID×4 inches long. The operating temperature of 1200° F. is much lower than the temperatures of the conventional oxidizers, which operate between 1600 and 2200° F., the higher temperatures being necessary due to the higher flow rates. Operating the thermal oxidizer at 1200° F. allows the thermal oxidizer heater element to have a much longer operating life than higher temperature oxidizers and this benefit is made possible by the lower flow rates possible with electrochemical sensors.

From the thermal oxidizer, the converted stack gas flows to the $SO_2$ electrochemical sensor 66 installed in the teflon manifold embedded into the aluminum housing. The aluminum housing is thermoelectrically temperature controlled to 65° F., with the temperature being sensed and controlled by the TRS electronics control 38 which is adjustable between 35 and 90° F. Both the heat exchanger temperature control and the sensor temperature control can heat or cool as required to maintain the set temperature. Maintaining the heat exchanger at 50° F. and the sensors at 65° F. causes the stack gas flowing to the $SO_2$ sensor to be at a constant relative humidity of approximately 50%. This relative humidity insures that the sensors do not dry out while also insuring that the stack gas is dry enough to prevent condensation on the sensor membrane. The heat exchanger and sensor temperatures may be set to achieve any controlled humidity level between 10 and 100%, as desired. Controlling the sensor to a constant temperature also has the added benefit of eliminating the temperature related drift of the electrochemical sensor. Controlling both the electrochemical sensor temperature and humidity is the key to long term analyzer stability and low maintenance.

From the output of the SO$_2$ sensor, the stack gas flows through orifice protection filter 72 and to eductor 75 and to vent at point 78.

The stack gas at point 40 flows in a parallel circuit to the oxygen sensor 44 which is also an electrochemical sensor. The relative humidity of the gas stream and temperature of the O$_2$ sensor is maintained and controlled in the same manner as the SO$_2$ sensor. From the O$_2$ sensor, the stack gas flows through orifice protection filter 70 and through sample eductor 75 to vent at point 78.

The preceding description has described a method of sample conditioning and temperature control that allows electrochemical sensors to accurately and reliably measure TRS and O$_2$. This method would also enhance the operation of electrochemical sensors measuring many gases such as H$_2$S, CO, NO, NO$_2$, Cl$_2$, HCN, HCl and NH$_3$. Due to the gas cross-sensitivity problems associated with electrochemical sensors, different gas scrubbers or filters would need to be used, but the basic method of humidity and temperature control could be applied to all the sensors mentioned above.

What is claimed is:

1. A method for analyzing gas flowing through a stack for total reduced sulfur, comprising the steps of:
    a) withdrawing at a rate of about 10–200 cc/min, a portion of the gas flowing through the stack;
    b) filtering the withdrawn gas;
    c) passing the filtered gas to a first zone regulated to a temperature T$_1$ and regulating the temperature of the filtered gas to T$_1$ by passing through a tube regulated to T$_1$ by a heat exchanger, the filtered gas having a relative humidity of 50–100% at T$_1$;
    d) splitting the temperature regulated gas into first and second portions;
    e) scrubbing SO$_2$ from the first portion within said first zone at temperature T$_1$ by passing through a column containing SO$_2$ scrubber media within said first zone and at temperature T$_1$;
    f) subjecting the first portion of the scrubbed gas to oxidizing conditions to convert total reduced sulfur compounds therein to SO$_2$;
    g) passing the converted gas to a second zone controlled to a temperature T$_2$ which is greater than or equal to T$_1$, such that the relative humidity of the converted gas in the second zone is less than 100%, and analyzing the converted gas by means of a first electrochemical sensor maintained at temperature T$_2$;
    h) passing the second portion of the scrubbed gas to said second zone at temperature T$_2$, the relative humidity of the second portion in the second zone being less than 100%, and analyzing the second portion for oxygen by means of a second electrochemical sensor maintained at temperature T$_2$; and
    i) determining total reduced sulfur in the gas, said steps b), c), d), e), f), g) and h) taking place within a common instrument housing.

2. A method according to claim 1, additionally comprising regulating gas and scrubber temperatures by locating the tube and the scrubbing column in a common, temperature regulated housing.

3. A method according to claim 2, wherein the housing temperature is regulated thermoelectrically.

4. A method according to claim 1, additionally comprising providing two parallel scrubbing columns, and utilizing one column for scrubbing SO$_2$ from the temperature regulated gas, and cleaning the other column with a flow of cleaning gas.

5. A method according to claim 1, wherein the oxidizing conditions comprise a temperature of about 1200° F.

6. A method according to claim 1, wherein said rate is about 50 cc/min.

7. A method according to claim 1, wherein said first and second portions are substantially equal.

8. A method according to claim 1, wherein T$_1$ is regulated to about 35° to about 90° F.

9. A method according to claim 8, wherein T$_1$ is regulated to about 50° F.

10. A method according to claim 1, wherein the scrubbed gas has a relative humidity of about 100%.

11. A method according to claim 10, wherein T$_2$ is maintained at a temperature such that the gases analyzed have a relative humidity of about 10 to 100%.

12. A system for analyzing stack gas comprising a common instrument housing containing therein:
    a) a probe extending from the housing into a stack for withdrawing a portion of the stack gas therefrom;
    b) a filter for removing particulate matter from the withdrawn stack gas operatively connected to said probe;
    c) first heat exchanger means operating to create a first zone regulated to temperature T$_1$, said first zone containing therein a temperature regulated tube operatively connected to said filter, and regulating the temperature of the filtered stack gas, and means for draining water condensed from the temperature regulated gas;
    d) gas splitting means operatively connected to said temperature regulated tube for splitting the scrubbed gas into first and second portions;
    e) a scrubber means operatively connected to said gas splitting means for scrubbing SO$_2$ from the first portion;
    f) oxidizer means operatively connected to said scrubber means for oxidizing total reduced sulfur compounds in a first gas portion; and
    g) second heat exchanger means operating to create a second zone regulated to a temperature T$_2$, equal to or greater than T$_1$, said second zone containing therein first and second electrochemical sensors regulated to temperature T$_2$, said first electrochemical sensor being operatively connected to said oxidizer means for determining SO$_2$ in the oxidized first gas portion, and said second electrochemical sensor being operatively connected to said splitting means for determining oxygen in the second gas portion.

13. A system according to claim 12, additionally comprising means for blowing cleaning gas through said sampling probe, and simultaneously blowing cleaning gas through said tube to cause drainage of condensed liquid.

14. A system according to claim 12, wherein said first heat exchanger means comprises two substantially vertical tubes connected at a bottom portion thereof to from a reservoir for draining condensed water.

15. A system according to claim 12, wherein the first heat exchanger means and scrubber means are located in a common, temperature-regulated housing.

16. A system according to claim 15, additionally comprising thermoelectric means for regulating the temperature of the housing containing the first heat exchanger means and the scrubber means.

17. A system according to claim 12, wherein said scrubber means comprises a pair of columns containing a scrubbing media, and means for passing temperature-regulated gas through one tube for scrubbing while passing cleaning gas through the other column.

18. A system according to claim 12, wherein said first and second electrochemical sensors are located in a common, temperature-regulated housing.

19. A system according to claim 18, additionally comprising thermoelectric means for regulating the temperature of the housing containing the sensors.

20. A system according to claim 12, additionally comprising a control means for controlling the temperatures of the first and second heat exchanger means, the scrubber means and the electrochemical sensors.

* * * * *